United States Patent
Kanai et al.

(10) Patent No.: US 9,041,928 B2
(45) Date of Patent: *May 26, 2015

(54) FEATURE VALUE ESTIMATION DEVICE AND CORRESPONDING METHOD, AND SPECTRAL IMAGE PROCESSING DEVICE AND CORRESPONDING METHOD

(75) Inventors: Masashi Kanai, Azumino (JP); Yoshifumi Arai, Matsumoto (JP)

(73) Assignee: SEIKO EPSON CORPORATION, Tokyo (JP)

(*) Notice: Subject to any disclaimer, the term of this patent is extended or adjusted under 35 U.S.C. 154(b) by 281 days.

This patent is subject to a terminal disclaimer.

(21) Appl. No.: 13/472,047

(22) Filed: May 15, 2012

(65) Prior Publication Data
US 2012/0293801 A1   Nov. 22, 2012

(30) Foreign Application Priority Data
May 20, 2011 (JP) ................................. 2011-113483

(51) Int. Cl.
G01J 3/46 (2006.01)
G01N 33/02 (2006.01)
G01N 21/25 (2006.01)
G01N 21/27 (2006.01)
G01N 21/31 (2006.01)

(52) U.S. Cl.
CPC ............ *G01N 33/025* (2013.01); *G01N 21/251* (2013.01); *G01N 21/274* (2013.01); *G01N 2021/3196* (2013.01)

(58) Field of Classification Search
USPC ................................................ 356/402–425
See application file for complete search history.

(56) References Cited

U.S. PATENT DOCUMENTS

| 5,929,906 A | 7/1999 | Arai et al. |
| 8,587,783 B2 * | 11/2013 | Arai .............................. 356/421 |
| 2008/0123097 A1 * | 5/2008 | Muhammed et al. ......... 356/419 |

FOREIGN PATENT DOCUMENTS

| JP | H09-163382 A | 6/1997 |
| JP | H10-173941 A | 6/1998 |
| JP | A-2001-099710 | 4/2001 |
| JP | 2005-274238 A | 10/2005 |
| JP | 2006-250827 A | 9/2006 |
| JP | A-2007-108124 | 4/2007 |
| JP | 2010-156612 A | 7/2010 |
| WO | 2005/111583 A1 | 11/2005 |

OTHER PUBLICATIONS

Ueno, Souichirou et al, "Development of the freshness checker," Memoirs of the Hokkaido Institute of Technology, vol., No. 35, pp. 313-317, Mar. 26, 2007.

* cited by examiner

Primary Examiner — Abdullahi Nur
(74) Attorney, Agent, or Firm — Oliff PLC (57) ABSTRACT

An estimation device is configured to estimate a feature value of a specific component contained in a sample and includes: a spectral estimation parameter storage module; a calibration parameter storage module; a multiband image acquirer; an optical spectrum operator configured to compute an optical spectrum from a multiband image using a spectral estimation parameter; and a calibration processor configured to compute the feature value from the optical spectrum using a calibration parameter.

7 Claims, 6 Drawing Sheets

FEATURE VALUE ESTIMATION DEVICE AND CORRESPONDING METHOD, AND SPECTRAL IMAGE PROCESSING DEVICE AND CORRESPONDING METHOD

CROSS REFERENCE TO RELATED APPLICATIONS

The present application claims the priority based on Japanese Patent Application No. 2011-113483 filed on May 20, 2011, the disclosure of which is hereby incorporated by reference in its entirety.

BACKGROUND

1. Technical Field

The present invention relates to estimating the feature value of a specific component contained in a sample and obtaining the optical spectrum from a multiband image.

2. Description of the Related Art

One proposed structure of a freshness sensor used to evaluate the freshness of fresh foods includes a spectroscope configured to disperse the reflected light from a sample. This prior art freshness sensor converts the reflectance spectrum as the output of the spectroscope into an electric signal by means of an imaging element and compares the electrical signal converted from the reflectance spectrum with a standard spectrum to evaluate the freshness of the sample.

The reflectance spectrum output from the spectroscope represents a feature value of the sample, so that the feature value of the sample can be estimated by utilizing the reflectance spectrum.

This prior art structure enables highly-accurate estimation of the feature value, but requires an expensive, high-performance spectroscope with high wavelength resolution and high S/N ratio, which leads to cost increase.

SUMMARY

Consequently, by taking into account the above problems, there is a need to enable highly-accurate estimation of the feature value without requiring any expensive high-performance spectroscope.

In order to achieve at least part of the foregoing, the present invention provides various aspects and embodiments described below.

According to a first aspect, there is provided An estimation device configured to estimate a feature value of a specific component contained in a sample. The estimation device includes: a spectral estimation parameter storage module configured to store a spectral estimation parameter used to convert a plurality of band images in different wavelength bands into an optical spectrum; a calibration parameter storage module configured to store a calibration parameter used to convert the optical spectrum into the feature value; a multiband image acquirer configured to obtain a multiband image of the sample taken in a plurality of wavelength bands including at least a specified wavelength band for the specific component; an optical spectrum operator configured to compute the optical spectrum from the multiband image using the spectral estimation parameter stored in the spectral estimation parameter storage module; and a calibration processor configured to compute the feature value from the optical spectrum computed by the optical spectrum operator using the calibration parameter stored in the calibration parameter storage module.

The estimation device according to the first aspect computes the optical spectrum from the multiband image of the sample taken in the plurality of wavelength bands including at least the specified wavelength band for the specific component of the sample, using the spectral estimation parameter and computes the feature value of the sample from the optical spectrum using the calibration parameter. In the estimation device of this aspect, only providing the spectral estimation parameter and the calibration parameter in advance enables the high-accurate estimation of the feature value of the sample from the multiband image without requiring any expensive high-performance spectroscope.

According to one embodiment, there is provided the estimation device, wherein the multiband image acquirer may include: a measurement optical wavelength band data storage module configured to store a plurality of measurement optical wavelength band data used for giving specification of a measurement optical wavelength band to a multiband camera, which is used to take an image of the sample with sensitivity of a plurality of wavelength bands; and a measurement optical wavelength band specifier configured to give specification of the measurement optical wavelength band to the multiband camera by sending the measurement optical wavelength band data stored in the measurement optical wavelength band data storage module to the multiband camera.

The estimation device according to this embodiment is configured to give specification of the measurement optical wavelength band to the multiband camera, thus ensuring acquisition of the multiband image taken in the plurality of wavelength bands including the specified wavelength band for the specific component.

According to another embodiment, there is provided the estimation device of giving specification of the measurement optical wavelength band, which may further include: a preprocessing data storage module configured to store preprocessing data, which specifies a correction amount used to correct an error in the multiband camera, from which the multiband image is obtained, with respect to each of band images constituting the multiband image; and a preprocessor configured to correct the multiband image obtained by the multiband image acquirer, based on the preprocessing data stored in the preprocessing data storage module, and send the corrected multiband image to the optical spectrum operator.

The estimation device according to this embodiment is configured to correct the error in the multiband camera, thus further improving the estimation accuracy.

According to yet another embodiment, there is provided the estimation device of performing the preprocessing, which may further include: a diagnostic data storage module configured to store diagnostic data used to convert the feature value of the sample to an evaluation value of the sample; and an evaluator configured to compute the evaluation value of the sample from the feature value computed by the calibration processor, based on the diagnostic data stored in the diagnostic data storage module.

The estimation device according to this embodiment is configured to compute the valuation value of the sample from the computed feature value.

According to a second aspect, there is provided a spectral image processing device configured to convert a plurality of band images in different wavelength bands into an optical spectrum. The spectral image processing device includes: a spectral estimation parameter storage module configured to store a spectral estimation parameter indicating a relationship between a first set of variables showing pixel values at a specific position in the plurality of band images and a second set of variables showing an optical spectrum at a location of a sample corresponding to the specific position; a multiband image acquirer configured to obtain a multiband image of the sample taken in a plurality of wavelength bands; and an optical spectrum operator configured to compute the optical spectrum from the multiband image using the spectral estimation parameter stored in the spectral estimation parameter storage module.

The spectral image processing device according to the second aspect computes the optical spectrum from the multiband image of the same taken in the plurality of wavelength bands, using the spectral estimation parameter. In the spectral image processing device of this aspect, only providing the spectral estimation parameter enables the optical spectrum to be obtained from the multiband image without requiring any expensive high-performance spectroscope.

According to a third aspect, there is provided a feature value estimation method of estimating a feature value of a specific component contained in a sample. The feature value estimation method obtains a multiband image of the sample taken in a plurality of wavelength bands including at least a specified wavelength band for the specific component; computes an optical spectrum from the multiband image using a spectral estimation parameter used to convert a plurality of band images in different wavelength bands into the optical spectrum; and computes the feature value from the computed optical spectrum using a calibration parameter used to convert the optical spectrum into the feature value.

According to a fourth aspect, there is provided a spectral image processing method of converting a plurality of band images in different wavelength bands into an optical spectrum. The spectral image processing method obtains a multiband image of a sample taken in a plurality of wavelength bands; and computes the optical spectrum from the multiband image using a spectral estimation parameter indicating a relationship between a first set of variables showing pixel values at a specific position in the plurality of band images and a second set of variables showing an optical spectrum at a location of the sample corresponding to the specific position.

Like the estimation device according to the first aspect, the feature value estimation method according to the third aspect enables highly-accurate estimation of the feature value of the sample from the multiband image without requiring any expensive high-performance spectroscope. Like the spectral image processing device according to the second aspect, the spectral image processing method according to the fourth aspect enables the optical spectrum to be obtained from the multiband image without requiring any expensive high-performance spectroscope.

The present invention may be implemented by a variety of aspects and applications, other than those described above, for example, a freshness evaluation system including the estimation device with the multiband camera.

For example, according to one aspect of the invention, there is provided a device including at least one element among five elements, i.e., a first storage module, a second storage module, an image acquirer, an operator and a processor. In other words, this device may include or may not include the first storage module. This device may include or may not include the second storage module. This device may include or may not include the image acquirer. This device may include or may not include the operator. This device may include or may not include the processor. The first storage module may be configured to, for example, store a spectral estimation parameter used to convert a plurality of band images in different wavelength bands into an optical spectrum. The second storage module may be configured to, for example, store a calibration parameter used to convert the optical spectrum into a feature value. The image acquirer may be configured to, for example, obtain a multiband image of a sample taken in a plurality of wavelength bands including at least a specified wavelength band for a specific component. The operator may be configured to, for example, compute the optical spectrum from the multiband image using, for example, the spectral estimation parameter. The processor may be configured to, for example, compute the feature value from the optical spectrum computed by the optical spectrum operator using, for example, the calibration parameter. This device may be implemented as, for example, the feature amount estimation device but may also be implemented as any of various devices other than the feature amount estimation device. This aspect has at least one of advantageous effects including size reduction of the device, cost saving, resource saving, easy manufacturing, and improved convenience. Part or all of the technical matters according to the respective embodiments of the feature amount estimation device described above may be applied to this device.

For example, according to one aspect of the invention, there is provided a device including at least one element among three elements, i.e., a storage module, a image acquirer, and an operator. In other words, this device may include or may not include the storage module. This device may include or may not include the image acquirer. This device may include or may not include the operator. The storage module may be configured to, for example, store a spectral estimation parameter indicating a relationship between a first set of variables showing pixel values at a specific position in a plurality of band images and a second set of variables showing an optical spectrum at a location of a sample corresponding to the specific position. The image acquirer may be configured to, for example, obtain a multiband image of the sample taken in a plurality of wavelength bands. The operator may be configured to, for example, compute the optical spectrum from the multiband image using the spectral estimation parameter stored in the spectral estimation parameter storage module. This device may be implemented as, for example, the spectral image processing device but may also be implemented as any of various devices other than the spectral image processing device. This aspect has at least one of advantageous effects including size reduction of the device, cost saving, resource saving, easy manufacturing, and improved convenience. Part or all of the technical matters according to the respective embodiments of the spectral image processing device described above may be applied to this device.

DESCRIPTION OF THE PREFERRED EMBODIMENTS

The invention is described in detail with reference to some embodiments. One embodiment of the invention is configured to evaluate the freshness of a sample of a green vegetable. The green vegetable may be, for example, spinach, Japanese mustard spinach (komatsuna) or green pepper.

A. General Configuration of Freshness Evaluation System

Figure 1:
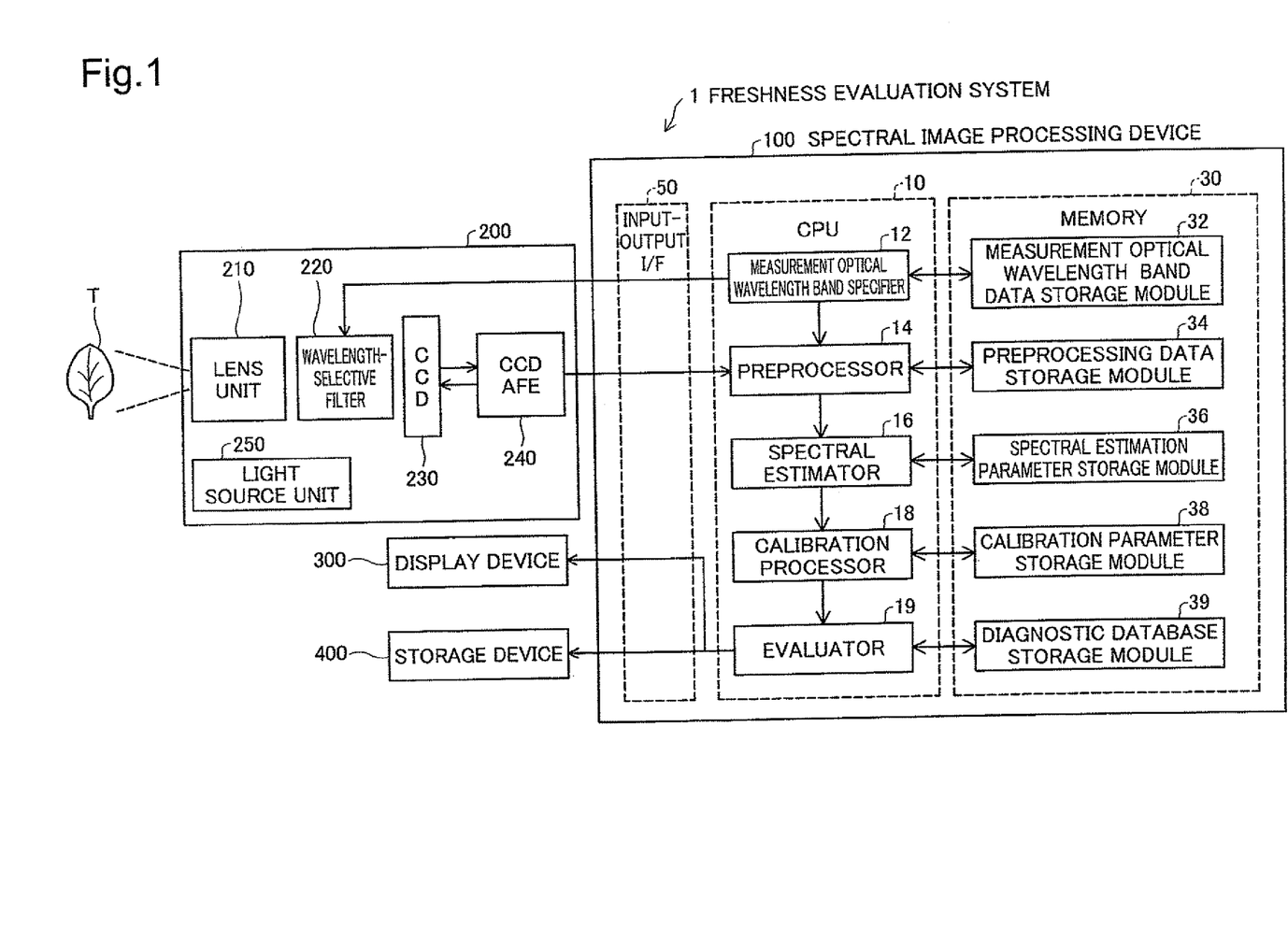
FIG. 1 illustrates the general configuration of a freshness evaluation system according to one embodiment of the invention.

FIG. 1 illustrates the general configuration of a freshness evaluation system 1 according to one embodiment of the invention. As illustrated, the freshness evaluation system 1 includes a spectral image processing device 100, a multiband camera 200, a display device 300 and a storage device 400. The multiband camera 200, the display device 300 and the storage device 400 are electrically connected with the spectral image processing device 100.

The multiband camera 200 includes a lens unit 210, a wavelength-selective filter 220, a CCD (charge-coupled device) 230, a CCDAFE (analog front end) 240, and a light source unit 250. The lens unit 210 is not provided with the auto-focusing mechanism to focus on a subject according to this embodiment, but may be provided with the auto-focusing mechanism. The wavelength-selective filter 220 used in this embodiment is a Fabry-Perot filter having a variable transparent wavelength range. The CCD 230 serves as an imaging device to perform photoelectric conversion of the light transmitted through the wavelength-selective filter 220 and obtain an electrical signal representing an image of the subject. The CCDAFE 240 serves to digitize the detection signal of the CCD 230. The light source unit 250 serves to illuminate the subject.

In the multiband camera 200 of this structure, the wavelength-selective filter 220 sequentially receives specification of a plurality of measurement optical wavelength bands from the spectral image processing device 100, so as to sequentially change its transparent wavelength range. The multiband camera 200 accordingly takes an image of a sample T (subject) at the sensitivity of the plurality of wavelength bands (multiband).

The display device 300 serves to display information on its screen. The storage device 400 serves as an external device to store data and may be, for example, a hard disk drive.

The spectral image processing device 100 processes a multiband image taken by the multiband camera 200 to evaluate the freshness of the sample T. The spectral image processing device 100 includes a CPU 10 configured to execute programs to implement various operations and controls, a memory 30 configured to store programs, data and information, and an input-output interface (I/F) 50 configured to receive image data from the multiband camera 200 and output the result of freshness evaluation to the display device 300 and the storage device 400.

The memory 30 has a measurement optical wavelength band data storage module 32, a preprocessing data storage module 34, a spectral estimation parameter storage module 36, a calibration parameter storage module 38, and a diagnostic database storage module 39. The details of the respective storage modules 32 to 39 will be described later. The memory 30 also has a program storage module (not shown) to store a freshness evaluation program. According to this embodiment, the memory 30 is a non-volatile memory. The non-volatile memory may alternatively be replaced with a volatile memory to store externally received data and parameters required for processing.

The CPU 10 executes the freshness evaluation program stored in the program storage module of the memory 30 to serve as a measurement optical wavelength band specifier 12, a preprocessor 14, a spectral estimator 16, a calibration processor 18, and an evaluator 19. The respective functional blocks 12 to 19 perform the relevant operations with the data and the parameters stored in the corresponding storage modules 32 to 39. As the results of the respective operations, the CPU 10 obtains a multiband image taken with the multiband camera 200, evaluates the freshness of the sample T based on the obtained multiband image and sends the result of freshness evaluation to the display device 300 and the storage device 400 via the input-output I/F 50. The result of freshness evaluation is accordingly displayed and stored.

The spectral image processing device 100 estimates the feature value of a specific component contained in the sample T in the process of evaluating the freshness of the sample T, and thereby also serves as the estimation device. The input-output interface (I/F) 50, the measurement optical wavelength band data storage module 32 of the memory 30 and the function of the measurement optical wavelength band specifier 12 implemented by the CPU 10 correspond to the "multiband image acquirer" described in Summary section above. The diagnostic database storage module 39 corresponds to the "diagnostic data storage module" described in Summary section above.

B. Procedure of Freshness Evaluation

Figure 2:
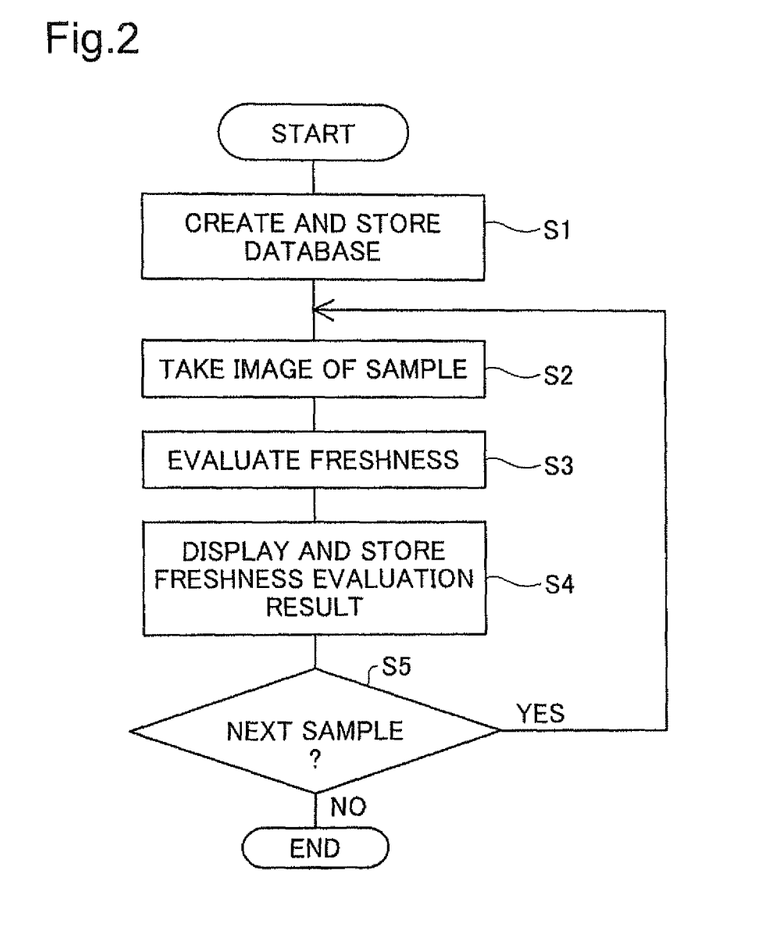
FIG. 2 is a flowchart showing a procedure of evaluating the freshness of a green vegetable.

FIG. 2 is a flowchart showing the procedure of evaluating the freshness of the green vegetable. As illustrated, the procedure first creates a database required for freshness evaluation and stores the created database in the memory 30 of the spectral image processing device 100 (step S1). The database herein corresponds to the various data stored in the respective storage modules 32 to 39 in the spectral image processing device 100 (FIG. 1).

The procedure subsequently uses the multiband camera 200 connected with the spectral image processing device 100 to take an image of the sample T (step S2). The spectral image processing device 100 then evaluates the freshness of the sample T based on the multiband image output from the multiband camera 200 (step S3) and displays and stores the result of freshness evaluation (step S4). The spectral image processing device 100 then determines whether there is a next sample T to be processed (step S5). When there is a next sample T (step S5: Yes), the procedure returns to step S2 and performs the processing of steps S2 to S4 for the next sample T. When there is no next sample T (step S5: No), on the other hand, this procedure is terminated.

C. Creation and Storage of Database

The following describes the contents of various data created and stored in the form of the database at step S1 described above and the method of creating such data. The various data herein include measurement optical wavelength band data, preprocessing data, spectral estimation parameters, calibration parameters and a diagnostic database. The database is preferably created and stored before factory shipment of the spectral image processing device 100. The freshness evaluation of step S3 may be omitted when the sample T of known freshness is used. The operator or user may perform part of the above procedure via a user interface (not shown).

Measurement Optical Wavelength Band Data

When the green vegetable is old, the vivid green color is faded with degradation of chlorophyll. This indicates that the freshness of the green vegetable can be evaluated from the amount of chlorophyll. The procedure of this embodiment estimates the amount of chlorophyll as the feature value of the sample and thereby evaluates the freshness of the sample of the green vegetable.

Figure 3:
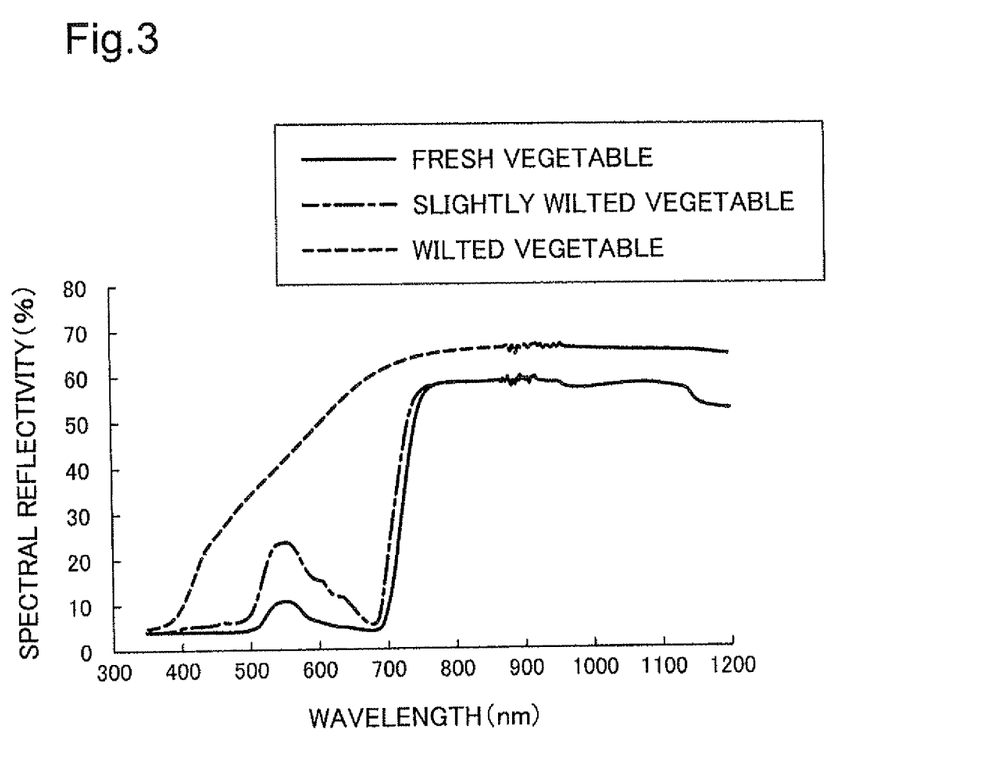
FIG. 3 is a graph showing the variations in spectral reflectivity against the wavelength of light with respect to green vegetables having different degrees of freshness.

FIG. 3 is a graph showing the variations in spectral reflectivity against the wavelength of light with respect to the green vegetables having different degrees of freshness. As illustrated, the fresh vegetable (or the slightly wilted vegetable) has light absorption of chlorophyll at about 700 nm. A plurality of wavelengths in a optical wavelength range of 500 nm to 1100 nm including the wavelength of light absorption of chlorophyll (about 700 nm) are stored as measurement optical wavelength band data in the measurement optical wavelength band data storage module 32 and are used for giving specification of the measurement optical wavelength bands to the multiband camera 200. For example, 31 measurement optical wavelength band data at the intervals of 20 nm in the optical wavelength range of 500 nm to 1100 nm (more specifically, 500 nm, 520 nm, 540 nm, . . . , 1060 nm, 1080 nm and 1100 nm) may be stored.

The measurement optical wavelength band data is not limited to 31 data at the intervals of 20 nm but may include any plural number of data, e.g., 61 data at the intervals of 10 nm. The interval may not be fixed but may be varied, such that a specific optical wavelength band sufficiently close to about 700 nm as the wavelength of light absorption of chlorophyll may be divided at less intervals. The measurement optical wavelength band data is not limited to the optical wavelength range of 500 nm to 1100 nm but may be any other suitable optical wavelength range including the wavelength of light absorption of chlorophyll (about 700 nm).

Preprocessing Data

The multiband camera 200 generally has hardware manufacturing errors, e.g., unevenness in the optical system, the deflection of the Fabry-Perot filter used for the wavelength-selective filter 220, and the illumination variation of the light source unit 250. This causes the wavelength variation (variation in transparent wavelength) and the light intensity variation (variation in light intensity) in each plane or each band image of a multiband image taken with the multiband camera 200. According to this embodiment, correction amounts for cancelling out the in-plane wavelength variation and the in-plane light intensity variation are stored as the preprocessing data in the preprocessing data storage module 34.

More specifically, the procedure first takes and obtains a multiband image of a uniform color sample with the multiband camera 200 (at least the same model or more preferably the actual machine) used for freshness evaluation. The procedure subsequently determines correction data with respect to each pixel for cancelling out the hardware manufacturing errors, so as to ensure the evenness at any position in each plane or band image of the multiband image. Each set of correction data with respect to the respective pixels is stored as preprocessing data corresponding to each plane or band image of the multiband image in the preprocessing data storage module 34. The uniform color sample preferably has the color that makes even reflection of light in any wavelength range and is, for example, a standard whiteboard.

Figure 4:
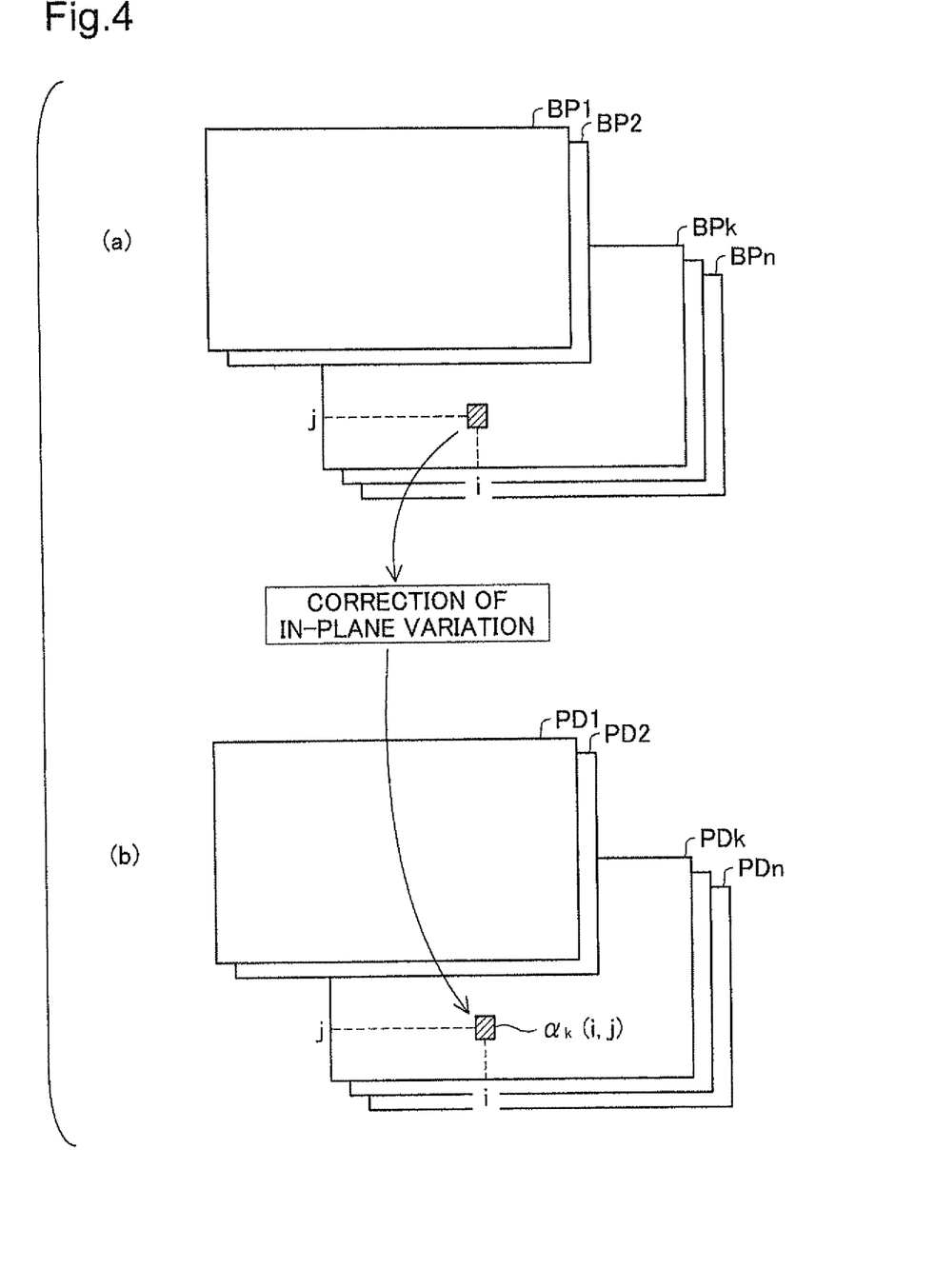
FIG. 4 illustrates an example of preprocessing data.

FIG. 4 illustrates an example of preprocessing data. The drawing (a) of FIG. 4 shows a multiband image, and the drawing (b) of FIG. 4 shows preprocessing data. As illustrated, a plurality of preprocessing data PD1, PD2, . . . , PDn are provided corresponding to respective band images BP1, BP2, . . . , BPn constituting the multiband image (i.e., corresponding to respective wavelength bands of the multiband image). The number of preprocessing data PD1, PD2, . . . , PDn provided is accordingly equal to the number of band images BP1, BP2, . . . , BPn. Each of the preprocessing data PD1, PD2, . . . , PDn has the same number of elements (the same number of pixels) as that of the corresponding band image. Correction data $\alpha_k(i,j)$ stored at a laterally i-th and vertically j-th element in k-th preprocessing data PDk (where k=1 to n) is correction data used to correct a laterally i-th and vertically j-th pixel in the corresponding k-th band image BPk and cancel out the unevenness in the k-th band image BPk.

According to this embodiment, the correction data are generated for all the pixels in the respective band images BP1 to BPn. According to another embodiment, correction data may be generated discretely and accordingly decreased in number, and interpolation operation may be performed with respect to pixels without correction data. The method of generating the preprocessing data is not limited to the above procedure but may be any other suitable method.

Spectral Estimation Parameters

The spectral estimation parameters represent the relationship between the multiband image and the optical spectrum. The multiband image is taken by the multiband camera 200 and consists of a plurality of band images in different wavelength bands. The optical spectrum is obtained by the spectroscope. More specifically, a spectral estimation matrix M in Equation (1) given below shows the spectral estimation parameters. In Equation (1), "x" represents a matrix of values (pixel values) at a specific position in the multiband image, and "p" represents a matrix of optical spectrum at a location corresponding to the specific position. The "pixel values at a specific position in the multiband image" mean the pixel values at the specific position in the respective band images constituting the multiband image. The "location corresponding to the specific position" means the location in the sample T corresponding to the specific position.

$$p = Mx \quad (1)$$

Equation (1) is rewritten as Equation (2) given below. As shown in Equation (2), the matrix x includes elements $x_1, x_2, \ldots, x_n$. Each of the elements corresponds to each of the measurement optical wavelength band data stored in the measurement optical wavelength band data storage module 32, and the number of elements "n" is equal to the number of measurement optical wavelength band data. The pixel value at the specific position in the multiband image is expressed by the light intensity in each measurement optical wavelength band, so that the matrix x of the pixel values is provided as the matrix x including the elements $x_1, x_2, \ldots, x_n$. The matrix p of the optical spectrum includes elements $p_1, p_2, \ldots, p_m$. Each of the elements corresponds to each wavelength band of the optical spectrum, and the number of elements "m" is greater than the number of elements "n" included in the matrix x of the pixel values in the multiband image. The spectral estimation matrix M is an m×n matrix.

$$\begin{pmatrix} p_1 \\ p_2 \\ \vdots \\ p_m \end{pmatrix} = \begin{pmatrix} m_{11} & m_{12} & \cdots & m_{1n} \\ m_{21} & m_{22} & & \\ \vdots & & \ddots & \vdots \\ m_{m1} & m_{m2} & \cdots & m_{mn} \end{pmatrix} \begin{pmatrix} x_1 \\ x_2 \\ \vdots \\ x_n \end{pmatrix} \quad (2)$$

A color sample provided in advance is subjected to imaging by the multiband camera 200 (at least the same model or more preferably the actual machine) used for freshness evaluation and an imaging device with a spectroscope (hereinafter called "spectral imaging device"). The spectral imaging device is known in the art, wherein the reflected light from the color sample passes through the spectroscope, and the spectrum output from the spectroscope is received on an imaging plane of an imaging element. Pixel values at a specific position are then extracted from a multiband image taken with the multiband camera 200. The specific position herein may be in any part of the multiband image actually including the image of the color sample but is preferably set corresponding to the location of the color sample detected to have less hardware manufacturing errors in the process of generating the preprocessing data.

The spectrum of reflected light from the location of the color sample corresponding to the specific position is extracted from the data obtained by the spectral imaging device. This results in providing the matrix x showing the pixel values at the specific position in the multiband image and the matrix p showing the optical spectrum at the location corresponding to the specific position, with respect to the color sample. The "pixel values at the specific position in the multiband image" is hereinafter called "pixel values of the multiband image", and the "location corresponding to the specific position" is hereinafter called "specific location".

A large number of color samples are provided across the wide optical wavelength band including visible optical wavelength range to infrared optical wavelength range and are subjected to imaging with the multiband camera and the spectral imaging device. The matrix x showing the pixel values of the multiband image and the matrix p showing the optical spectrum at the specific location are accordingly obtained with respect to each of the large number of color samples.

The matrix can generally be expressed by a vector, so that the matrix x and the matrix p are respectively expressed by a vector X and a vector P. A matrix $(X_1, X_2, \ldots, X_u)$ showing the pixel values of the multiband image with respect to the large number of color samples is correlated to a matrix $(P_1, P_2, \ldots, P_u)$ showing the optical spectrum at the specific location with respect to the large number of color samples by the spectral estimation matrix M according to Equation (3) given below. Here "u" is equal to the number of color samples.

$$(P_1, P_2, \ldots, P_u) = M(X_1, X_2, \ldots, X_u) \quad (3)$$

When the matrix $(X_1, X_2, \ldots, X_u)$ is expressed by A and the matrix $(P_1, P_2, \ldots, P_u)$ is expressed by B, Equation (3) is rewritten as Equation (4) given below. Equation (4) is further changed as Equation (5) given below.

$$B = MA \quad (4)$$

$${}^tM = (A^tA)^{-1}A^tB \quad (5)$$

In Equation (5), A represents the pixel values of the multiband image with respect to a plurality of color samples, and B represents the optical spectrum at the specific location with respect to the plurality of color samples. The matrix with the superscript "t" means the transposed matrix. The operator determines the spectral estimation matrix M according to Equation (5) and subsequently stores the determined spectral estimation matrix M as the spectral estimation parameters in the spectral estimation parameter storage module 36. The spectral estimation matrix M is determined, such that the left side and the right side of Equation (4) are sufficiently close to each other with respect to any of the color samples. One preferable procedure of determining the spectral estimation matrix M, enables the spectral estimation accuracy to be maintained with the less number of optical wavelength bands, as changing the measurement optical wavelength band of the multiband camera 200 and the number of optical wavelength bands. It is accordingly preferable to generate the spectral estimation parameters, simultaneously with generation of the measurement optical wavelength band data in the process of creating the database.

Color charts may be used for the color samples. The spectral estimation parameters are values depending on only the multiband camera and can thus be commonly used regardless of the variation in sample T or the variation in feature value.

The spectral estimation parameters are not limited to the details described above but may be any other values representing the relationship between the multiband image and the optical spectrum. The method of generating the spectral estimation parameters is not limited to the above procedure but may be any other suitable method.

Calibration Parameters

The calibration parameters represent the relationship between the optical spectrum and the feature value of the sample T. The feature value of the sample T means the amount of chlorophyll according to this embodiment. More specifically, a mixing matrix Z according to Equation (6) given below shows the calibration parameters. In Equation (6), "p" represents a matrix showing the optical spectrum at a specific location of the sample T of the green vegetable, and "s" represents the feature value at the specific location.

$$s = Zp \quad (6)$$

Equation (6) is rewritten as Equation (7) given below. As shown in Equation (7), the matrix p includes elements $p_1, p_2, \ldots, p_m$, and the matrix s includes elements $s_1, s_2, \ldots, s_l$. The mixing matrix Z is an l×m matrix. The number of elements "l" with respect to the feature value is generally less than the number of elements "m" with respect to the optical spectrum.

$$\begin{pmatrix} s_1 \\ \vdots \\ s_l \end{pmatrix} = \begin{pmatrix} z_{11} & z_{12} & \cdots & z_{1m} \\ \vdots & & \ddots & \vdots \\ z_{l1} & z_{l2} & \cdots & z_{lm} \end{pmatrix} \begin{pmatrix} p_1 \\ p_2 \\ \vdots \\ p_m \end{pmatrix} \quad (7)$$

A specific location of a green vegetable provided in advance is subjected to imaging with the spectral imaging device, and chlorophyll is extracted from a specific location of the green vegetable and is determined by chemical analysis. The "specific location" may be any part of the green vegetable, but it is preferable that the specific location subjected to imaging with the spectral imaging device is identical with the specific location as the target of the chemical determination. As the result of such imaging and chemical determination, the matrix p of the optical spectrum and the matrix s of the feature value are obtained with respect to the green vegetable. A large number of green vegetables with different degrees of freshness are provided, and each of the green vegetables is similarly subjected to imaging with the spectral imaging device and the chemical determination of chlorophyll. This gives the matrix p of the optical spectrum and the matrix s of the feature value with respect to each of the large number of green vegetables with different degrees of freshness.

The matrix can generally be expressed by a vector, so that the matrix p and the matrix s are respectively expressed by a vector P and a vector S. A matrix $(S_1, S_2, \ldots, S_w)$ showing the feature value with respect to the large number of green vegetables is correlated to a matrix $(P_1, P_2, \ldots, P_w)$ showing the optical spectrum with respect to the large number of green vegetables by the mixing matrix Z according to Equation (8) given below. Here "w" is equal to the number of green vegetables.

$$(S_1, S_2, \ldots, S_w) = Z(P_1, P_2, \ldots, P_w) \quad (8)$$

When the matrix $(P_1, P_2, \ldots, P_w)$ is expressed by C and the matrix $(S_1, S_2, \ldots, S_w)$ is expressed by D, Equation (8) is rewritten as Equation (9) given below. Equation (9) is further changed as Equation (10) given below.

$$D = ZC \quad (9)$$

$${}^tZ = ({}^tCC)^{-1}{}^tCD \quad (10)$$

In Equation (10), C represents the optical spectrum at the specific location with respect to a plurality of green vegetables with different degrees of freshness, and D represents the feature value at the specific location with respect to the plurality of green vegetables with different degrees of freshness. The operator determines the mixing matrix Z according to Equation (10) and stores the determined mixing matrix Z as calibration parameters in the calibration parameter storage module 38. The mixing matrix Z is determined, such that the left side and the right side of Equation (8) are sufficiently close to each other with respect to any of the green vegetables with different degrees of freshness.

The calibration parameters are not limited to the details described above but may be any other values representing the relationship between the optical spectrum and the feature value of the sample. The method of generating the calibration parameters is not limited to the above procedure but may be any other suitable method, such as principal component analysis, PLS analysis, or neural network-based technique.

Diagnostic Database

The diagnostic database represents the relationship between the feature value of the sample T and the freshness. The feature value of the sample T is expressed by the matrix D $(S_1, S_2, \ldots, S_w)$. The freshness is expressed by multiple levels, for example, A=excellent, B=good, and C=poor.

Figure 5:
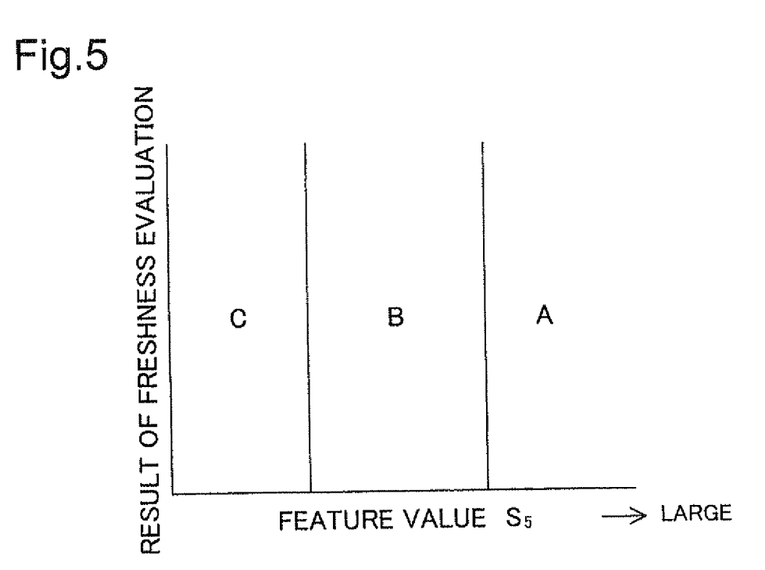
FIG. 5 is a graph showing one example of diagnostic database.

FIG. 5 is a graph showing one example of the diagnostic database. In this example, the freshness is evaluated among the multiple levels A, B and C corresponding to one of the elements in the matrix $(S_1, S_2, \ldots, S_w)$, for example, the element $S_5$.

Figure 6:
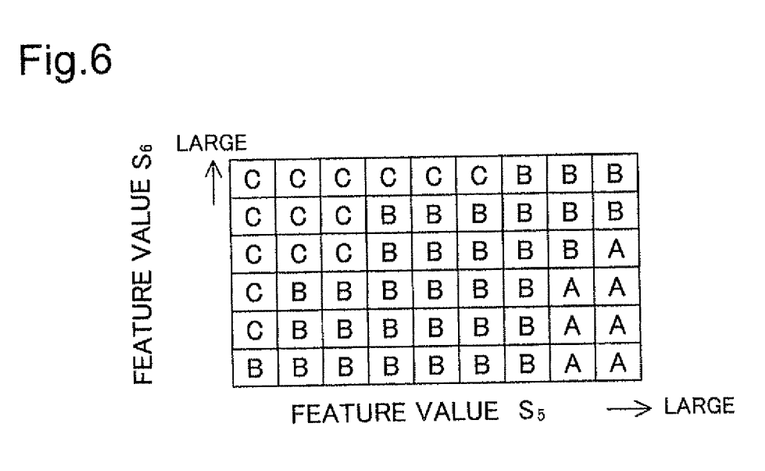
FIG. 6 is a graph showing another example of diagnostic database.

FIG. 6 is a graph showing another example of the diagnostic database. In this example, the freshness is evaluated among the multiple levels A, B and C corresponding to the combination of a plurality of elements n the matrix $(S_1, S_2, \ldots, S_w)$, for example, the combination of the elements $S_5$ and $S_6$. The plurality of elements is not limited to two but may be three or more. The multiple levels of the freshness is also not limited to three but may be two levels or four or more levels.

The foregoing describes the examples of the diagnostic database. The evaluation value is, however, not limited to the freshness but may be another sensory value, such as ripeness. In this latter case, the operator tastes the same kind of vegetables as the vegetable used for determining the calibration parameters and evaluates the flavor of each of the vegetables. A database is created by correlating the feature value to the evaluated flavor as the indication of the ripeness with respect to each kind of vegetable.

The diagnostic database is not limited to the details described above but may include any content representing the relationship between the feature value of the sample T and any suitable evaluation value.

D. Freshness Evaluation

The freshness evaluation process is described in detail. The freshness evaluation process is performed by the spectral image processing device 100 at steps S2 to S4 described above (FIG. 2). The CPU 10 executes the freshness evaluation program stored in the program storage module of the memory 30 to implement the freshness evaluation process.

Figure 7:
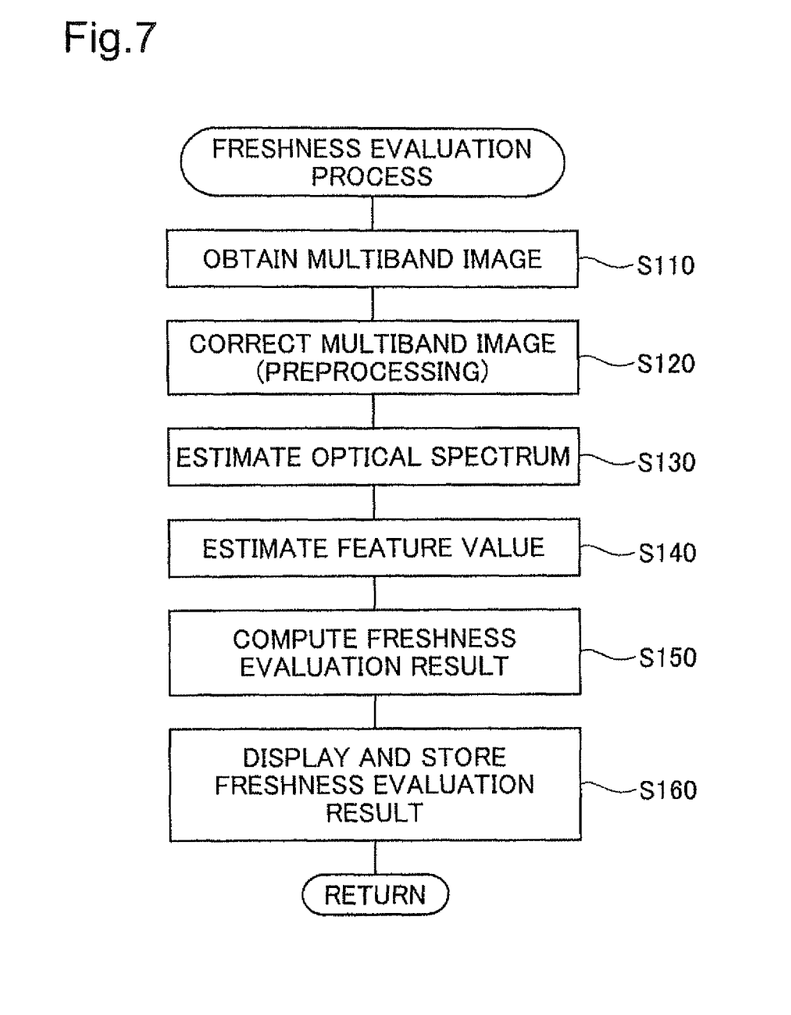
FIG. 7 is a flowchart showing a procedure of freshness evaluation process.

FIG. 7 is a flowchart showing the procedure of freshness evaluation process. As illustrated, on the start of the processing flow, the CPU 10 obtains a multiband image from the multiband camera 200 (step S110). More specifically, the CPU 10 sequentially sends a plurality of measurement optical wavelength band data stored in the measurement optical wavelength band data storage module 32 of the memory 30 to the wavelength-selective filter 220 of the multiband camera 200 to successively change the transparent wavelength range of the wavelength-selective filter 220 and thereby obtains a multiband image consisting of band images (spectral images) in different measurement optical wavelength bands from the multiband camera 200. The configuration of sending the plurality of measurement optical wavelength band data to the multiband camera 200 as part of the processing of step S110 corresponds to the function of the measurement optical wavelength band specifier 12 implemented by the CPU 10 (FIG. 1).

The CPU 10 subsequently performs preprocessing to correct the respective band images obtained at step S110 (step S120). The preprocessing herein represents image processing to correct the respective band images based on the preprocessing data for the respective wavelength bands stored in the preprocessing data storage module 34. For example, when the correction data of each of the elements constituting the k-th preprocessing data PDk is expressed by $\alpha_k(i,j)$ as illustrated in FIG. 4, the processing of step S120 corrects the pixel value $g_k(i,j)$ in the k-th band image according to Equation (11) given below.

$$tg_k(i,j) = \alpha_k(i,j) \cdot g_k(i,j) \quad (11)$$

where $tg_k(i,j)$ represents a pixel value after the correction.

Correcting the k-th band image with sequentially incrementing the variables "i" and "j" is repeated for all the band images from the 1st band image to the n-th band image, so that the entire multiband image is corrected. The correction data used as the preprocessing data implement the software cancellation of the hardware manufacturing errors of the multiband camera 200 as explained previously. The corrected multiband image accordingly includes correction of the wavelength variation and the light intensity variation due to the hardware manufacturing errors of the multiband camera 200.

Equation (11) given above is used for the correction data expressible as $\alpha_k(i,j)$. Correction follows Equation (12) given below, however, when the correction data is expressed by two variables $\alpha_k(i,j)$ and $\beta_k(i,j)$.

$$tg_k(i,j) = \alpha_k(i,j) \cdot g_k(i,j) + \beta_k(i,j) \quad (12)$$

where $tg_k(i,j)$ represents a pixel value after the correction.

The processing of step S120 described above corresponds to the function of the preprocessor 14 implemented by the CPU 10 (FIG. 1).

After the processing of step S120, the CPU 10 estimates an optical spectrum from the multiband image corrected at step S120 (hereinafter referred to as "corrected multiband image") (step S130). The estimation herein is based on the spectral estimation parameters stored in the spectral estimation parameter storage module 36.

More specifically, the arithmetic operation is performed according to Equation (1) described above. The optical spectrum p at the specific position is determinable by multiplying the spectral estimation parameters M stored in the spectral estimation parameter storage module 36 and the matrix x of the pixel values at the specific position in the corrected multiband image. The specific position herein may be any location of the multiband image actually including the image of the sample T, for example, the center position of the image. Any location of the multiband image is expected to give substantially the same result, since the wavelength variation and the light intensity variation have been corrected at step S120.

After the processing of step S130, the CPU 10 estimates the feature value of the sample T, i.e., the amount of chlorophyll, from the optical spectrum determined at step S130 (step S140). The estimation herein is based on the calibration parameters stored in the calibration parameter storage module 38.

More specifically, the arithmetic operation is performed according to Equation (6) described above. The feature value, i.e., the amount of chlorophyll, at the specific position is determinable by multiplying the calibration parameters Z stored in the calibration parameter storage module 38 and the matrix p of the optical spectrum at the specific position determined at step S130.

The processing of step S130 corresponds to the function of the spectral estimator 16 implemented by the CPU 10 (FIG. 1) and also corresponds to the "optical spectrum operator" described in Summary section above. The processing of step S140 corresponds to the function of the calibration processor 18 implemented by the CPU 10 (FIG. 1) and also corresponds to the "calibration processor" described in Summary section above.

After the processing of step S140, the CPU 10 computes the freshness evaluation result from the feature value estimated at step S140 (step S150). The computation of the freshness evaluation result herein is based on the diagnostic database stored in the diagnostic database storage module 39. More specifically, the freshness evaluation result may be computed by substituting the feature value $S_5$ estimated at step S140 into the graph of FIG. 5. Alternatively, the freshness evaluation result may be computed by substituting the feature quantities $S_5$ and $S_6$ estimated at step S140 into the graph of FIG. 6.

After the processing of step S150, the CPU 10 outputs the freshness evaluation result computed at step S150 to the display device 300 and the storage device 400 (step S160). The freshness evaluation result is accordingly displayed on the display device 300 and is stored in the storage device 400. After the processing of step S160, the CPU 10 goes to Return and terminates the current cycle of the freshness evaluation process. When there is any other sample T to be processed for freshness evaluation as described above with reference to FIG. 2, the CPU 10 repeats the freshness evaluation process.

E. Advantageous Effects of Embodiment

The freshness evaluation system 1 of the above configuration computes an optical spectrum from a multiband image of a green vegetable taken in a plurality of wavelength bands including a specified wavelength band where light absorption of chlorophyll is observed, using the spectral estimation parameters, and subsequently computes the amount of chlorophyll as the feature value from the optical spectrum using the calibration parameters. This configuration simply provides the spectral estimation parameter storage module 36 and the calibration parameter storage module 38 in the memory, so as to enable highly-accurate estimation of the amount of chlorophyll contained in the green vegetable from the multiband image without requiring any expensive high-performance spectroscope.

F. Modifications

The invention is not limited to the above embodiment or its applications but various modifications and variations may be made to the embodiment without departing from the scope of the invention. Some of possible modifications are described below, wherein the like components to those of the above embodiment are expressed by the like numerical symbols and are not specifically described here.

Modification 1

According to the above embodiment and its applications, the sample is a green vegetable, and the feature value is the amount of chlorophyll. According to another embodiment, the sample may be meat, and the feature value may be the amount of oleic acid. The amount of oleic acid can be used as the indication of the palatability of meat. According to yet another embodiment, the sample may be the human skin, and the feature value may be the amount of collagen. The amount of collagen can be used as the indication of the vitality of skin. In general, the sample may be any of foodstuffs, such as vegetables, fruits, meats and fish, human body components, such as skin and hair, and variety of other substances, and the feature value may be any of various specific components contained in such samples.

The sample and its feature value to be estimated may be readily changed by simply changing the databases or the data stored in the respective storage modules 32 to 39 in the freshness evaluation system 1 of the embodiment. In other words, the freshness evaluation system 1 of the embodiment has the general versatility.

Modification 2

According to the above embodiment and its applications, only the amount of chlorophyll as one specific component is estimated as the feature value. According to another embodiment, two feature quantities of two different specific components may be estimated; for example, the amount of chlorophyll and the amount of water.

Modification 3

The above embodiment uses the spectral image processing device 100 dedicated for the freshness evaluation system 1. The spectral image processing device 100 may be replaced by a general-purpose personal computer. The multiband camera 200 and the spectral image processing device 100 are provided as separate components according to the above embodiment, but may alternatively be integrated with each other. For example, the multiband camera 200 may be built in the spectral image processing device 100. In another example, the spectral image processing device 100 may be incorporated in the form of a chip in the multiband camera 200. The display device 300 and the storage device 400 may also be integrated with the spectral image processing device 100.

Modification 4

According to the above embodiment and its applications, the functions implemented by the software configuration may be implemented by the hardware configuration, for example, a discrete electronic circuit.

Modification 5

According to the above embodiment and its applications, the freshness evaluation system computes the optical spectrum from the multiband image using the spectral estimation parameters, and computes the feature value from the optical spectrum using the calibration parameters. According to another embodiment, the feature value may be estimated directly from the multiband image using parameters L (=Z·M) as the product of the matrix M of the spectral estimation parameters and the matrix Z of the calibration parameters. As long as the individual body of the multiband camera 200, the type of the sample T and the type of the feature value or the combination of feature quantities to be estimated are determined in advance, this modified configuration also enables highly-accurate estimation of the feature value of the sample from the multiband image without requiring any expensive high-performance spectroscope.

Modification 6

According to the above embodiment and its applications, the freshness evaluation system sequentially sends a plurality of measurement optical wavelength band data stored in the measurement optical wavelength band data storage module 32 to the wavelength-selective filter 220 of the multiband camera 200 to successively change the transparent wavelength range of the wavelength-selective filter 220 and thereby obtains a multiband image consisting of band images (spectral images) in different measurement optical wavelength bands from the multiband camera 200. According to another embodiment, a multiband image consisting of band images in a plurality of predetermined measurement optical wavelength bands may be obtained from the multiband camera 200. In other words, the measurement optical wavelength band data storage module 32 and the measurement optical wavelength band specifier 12 are not the essential elements of the spectral image processing device 100.

Modification 7

According to the above embodiment and its applications, the preprocessor 14 corrects the multiband image, based on the preprocessing data stored in the preprocessing data storage module 34, and the optical spectrum is estimated from the corrected multiband image. According to another embodiment, the optical spectrum may be estimated from the multiband image obtained by the multiband image acquirer. According to yet another embodiment, the multiband image acquirer may obtain the corrected multiband image. In other words, the preprocessing data storage module 34 and the preprocessor 14 are not the essential elements of the spectral image processing device 100.

Modification 8

According to the above embodiment and its applications, the evaluator 19 performs evaluation, based on the diagnostic database stored in the diagnostic database storage module 39 of the spectral image processing device 100 and the estimated feature value. According to another embodiment, the estimated feature value may be output to an evaluation device provided separately from the spectral image processing device 100, and the evaluation device may perform evaluation. In other words, the diagnostic database storage module 39 and the evaluator 19 are not essential elements of the spectral image processing device 100.

While the invention has been described with reference to exemplary embodiments thereof, it is to be understood that the invention is not limited only to the disclosed embodiments or constructions. On the contrary, the invention is intended to cover various modifications and equivalent arrangements. In addition, while the various elements of the disclosed invention are shown in various combinations and configurations, which are exemplary, other combinations and configurations, including fewer elements or only a single element, are also within the spirit and scope of the invention.

What is claimed is:

1. An estimation device configured to estimate a feature value of a specific component contained in a sample, comprising:
   a spectral estimation parameter storage module configured to store a spectral estimation parameter used to convert a plurality of band images in different wavelength bands into an optical spectrum;
   a calibration parameter storage module configured to store a calibration parameter used to convert the optical spectrum into the feature value;
   a multiband image acquirer configured to obtain a multiband image of the sample taken in a plurality of wavelength bands including at least a specified wavelength band for the specific component;
   an optical spectrum operator configured to compute the optical spectrum from the multiband image using the spectral estimation parameter stored in the spectral estimation parameter storage module; and
   a calibration processor configured to compute the feature value from the optical spectrum computed by the optical spectrum operator using the calibration parameter stored in the calibration parameter storage module.

2. The estimation device according to claim 1, wherein the multiband image acquirer comprises:
   a measurement optical wavelength band data storage module configured to store a plurality of measurement optical wavelength band data used for giving specification of a measurement optical wavelength band to a multiband camera, which is used to take an image of the sample with sensitivity of a plurality of wavelength bands; and
   a measurement optical wavelength band specifier configured to give specification of the measurement optical wavelength band to the multiband camera by sending the measurement optical wavelength band data stored in the measurement optical wavelength band data storage module to the multiband camera.

3. The estimation device according to claim 2, further comprising:
   a preprocessing data storage module configured to store preprocessing data, which specifies a correction amount used to correct an error in the multiband camera, from which the multiband image is obtained, with respect to each of band images constituting the multiband image; and
   a preprocessor configured to correct the multiband image obtained by the multiband image acquirer, based on the preprocessing data stored in the preprocessing data storage module, and send the corrected multiband image to the optical spectrum operator.

4. The estimation device according to claim 3, further comprising:
   a diagnostic data storage module configured to store diagnostic data used to convert the feature value of the sample to an evaluation value of the sample; and
   an evaluator configured to compute the evaluation value of the sample from the feature value computed by the calibration processor, based on the diagnostic data stored in the diagnostic data storage module.

5. A spectral image processing device configured to convert a plurality of band images in different wavelength bands into an optical spectrum, comprising:
- a spectral estimation parameter storage module configured to store a spectral estimation parameter indicating a relationship between a first set of variables showing pixel values at a specific position in the plurality of band images and a second set of variables showing an optical spectrum at a location of a sample corresponding to the specific position;
- a multiband image acquirer configured to obtain a multiband image of the sample taken in a plurality of wavelength bands;
- an optical spectrum operator configured to compute the optical spectrum from the multiband image using the spectral estimation parameter stored in the spectral estimation parameter storage module; and
- a preprocessing data storage module configured to store preprocessing data, which specifies a correction amount used to correct an error in a multiband camera, from which the multiband image is obtained, with respect to each of band images constituting the multiband image; and
- a preprocessor configured to correct the multiband image obtained by the multiband image acquirer, based on the preprocessing data stored in the preprocessing data storage module, and send the corrected multiband image to the optical spectrum operator.

6. A feature value estimation method of estimating a feature value of a specific component contained in a sample, the feature value estimation method comprising:
- obtaining a multiband image of the sample taken in a plurality of wavelength bands including at least a specified wavelength band for the specific component;
- computing an optical spectrum from the multiband image using a spectral estimation parameter used to convert a plurality of band images in different wavelength bands into the optical spectrum; and
- computing the feature value from the computed optical spectrum using a calibration parameter used to convert the optical spectrum into the feature value.

7. A spectral image processing method of converting a plurality of band images in different wavelength bands into an optical spectrum, the spectral image processing method comprising:
- obtaining a multiband image of a sample taken in a plurality of wavelength bands; and
- computing the optical spectrum from the multiband image using a spectral estimation parameter indicating a relationship between a first set of variables showing pixel values at a specific position in the plurality of band images and a second set of variables showing an optical spectrum at a location of the sample corresponding to the specific position;
- storing preprocessing data, which specifies a correction amount used to correct an error, with respect to each of band images constituting the multiband image; and
- correcting the multiband image obtained, based on the preprocessing data stored, and sending the corrected multiband image to be computed in the computing the optical spectrum.

* * * * *